(12) United States Patent
Qian et al.

(10) Patent No.: US 6,951,728 B2
(45) Date of Patent: Oct. 4, 2005

(54) MULTILAYER REAGENT TEST STRIPS TO QUANTIFY GLYCATED PROTEIN IN A PHYSIOLOGICAL SAMPLE

(75) Inventors: Suyue Qian, Fremont, CA (US); Shery Guo, San Jose, CA (US); Koon-wah Leong, Sunnyvale, CA (US)

(73) Assignee: LifeScan, Inc., Milpitas, CA (US)

( * ) Notice: Subject to any disclaimer, the term of this patent is extended or adjusted under 35 U.S.C. 154(b) by 445 days.

(21) Appl. No.: 10/144,562

(22) Filed: May 10, 2002

(65) Prior Publication Data
US 2003/0211564 A1 Nov. 13, 2003

(51) Int. Cl.$^7$ ................................................ C12Q 1/54
(52) U.S. Cl. .......................................... 435/14; 435/23
(58) Field of Search ........................... 422/60; 435/14, 435/23; 436/67, 95, 904

(56) References Cited

U.S. PATENT DOCUMENTS

| | | | |
|---|---|---|---|
| 5,470,752 A | | 11/1995 | Burd et al. |
| 5,695,949 A | | 12/1997 | Galen et al. |
| 5,725,774 A | | 3/1998 | Neyer |
| 6,008,006 A | | 12/1999 | Torrens et al. |
| 6,027,692 A | * | 2/2000 | Galen et al. ............. 422/82.05 |
| 6,127,138 A | * | 10/2000 | Ishimaru et al. .............. 435/23 |
| 6,677,158 B2 | * | 1/2004 | Hud et al. ..................... 436/67 |
| 6,743,597 B1 | * | 6/2004 | Guo et al. ..................... 435/14 |
| 2003/0211006 A1 | * | 11/2003 | Qian et al. .................... 422/56 |
| 2004/0121423 A1 | * | 6/2004 | Guo et al. ..................... 435/25 |

FOREIGN PATENT DOCUMENTS

| | | |
|---|---|---|
| EP | 0526150 | 2/1993 |
| EP | 0737744 A2 | 10/1996 |
| EP | 0821064 A2 | 1/1998 |
| EP | 0921 198 | 6/1999 |
| WO | WO96/31270 | 10/1996 |
| WO | WO96/31619 | 10/1996 |
| WO | WO96/34977 | 11/1996 |
| WO | WO 96/34977 | * 11/1996 |

OTHER PUBLICATIONS

Kobayashi K. et al., "A Novel Colorimetric Method for Determination of Glycated Protein Based on 2–Keto–Glucose Release with Hydrazine" Biological and Pharmaceutical Bulletin, Tokyo JP, vol. 16, No. 2, Feb. 1993, pp. 195–198.

* cited by examiner

*Primary Examiner*—Ralph Gitomer
(74) *Attorney, Agent, or Firm*—Carol M. LaSalle; Bozicevic, Field & Francis LLP (57) ABSTRACT

Multilayer reagent test strips for quantitating glycated protein in a fluid sample, as well as methods for using the same, are provided. The subject multilayer test strips include at least a filter layer, a proteinase layer and a ketoamine oxidase signal producing and fluid flow control system layer. In using the subject test strips, a fluid sample is applied to the test strip and a signal is generated that can be employed to quantitate the glycated protein level in the sample. The quantitated glycated protein level can then be employed to determine the amount of glycated protein in the fluid sample. Also provided are kits and systems that include the subject test strips and find use in practicing the subject methods. The subject compositions and methods find use in glycated protein monitoring applications, among other utilities.

15 Claims, 3 Drawing Sheets

MULTILAYER REAGENT TEST STRIPS TO QUANTIFY GLYCATED PROTEIN IN A PHYSIOLOGICAL SAMPLE

FIELD OF THE INVENTION

The field of this invention is analyte detection, particularly glycated protein detection.

BACKGROUND OF THE INVENTION

Individuals suffering from diabetes mellitus have an abnormally high blood sugar level generally because the pancreas does not secrete sufficient amounts of the active hormone insulin into the bloodstream to regulate carbohydrate metabolism. If an abnormally high blood sugar level, known as a hyperglycemic condition, is allowed to continue for prolonged periods, the individual will suffer from the chronic complications of diabetes, including retinopathy, nephropathy, neuropathy and cardiovascular disease. Studies indicate that diabetic patients who are able to maintain near normal glycemic control greatly reduce the likelihood of these dire complications. Therefore, several tests have been developed to measure and control glycemic condition.

One common medical test to control glycemic condition is the direct measurement of blood glucose levels by diabetics. Because blood glucose levels fluctuate significantly throughout a given day, being influenced by diet, activity, and treatment, depending on the nature and severity of the individual case, some patients measure their blood glucose levels up to seven times a day. Based on the observed pattern in the measured glucose levels, the patient and physician together make adjustments in diet, exercise and insulin intake to better manage the disease. Clearly, this information should be available to the patient immediately.

However, because of the frequent fluctuation of glucose levels in a given day, tests which are independent of a patient's diet, activity, and/or treatment and which provide longer term indications of blood glucose levels have also been developed. These tests measure the concentration of glycated proteins or "protein-bound glucose" (PBG). Proteins, such as those present in whole blood, serum and other biological fluids react with glucose, under non-enzymatic conditions, to produce glycated proteins. The extent of the reaction is directly dependent upon the glucose concentration of the blood.

One of the first glycated protein tests developed measures glycated hemoglobin, namely Hemoglobin $A_{1c}$ ($HbA_{1c}$), which reflects glycemic control over approximately a 2 to 3 month period. Other such tests measure serum proteins, such as total glycated serum protein, or a specific glycated serum protein, namely glycated albumin. Glycated albumin reflects an intermediate glycemic control over approximately a 2 to 3 week period.

Yet another way to indirectly assess blood sugar concentration is to analyze glycated protein concentration. The plasma proteins are glycated in vivo by a non-enzymatic reaction between glucose and available amino groups of blood proteins, principally the γ-amino groups of lysine residues and the α-amino groups of the protein's terminal amino acid. The glucose binds to an amino group of the protein to form a Schiff base, i.e., aldimine, that undergoes molecular rearrangement to form a stable ketoamine. In the art, such ketoamines are generically known as "fructosamines." The degree of protein glycation and fructosamine formation is directly proportional to blood glucose concentration. Measurement of serum or plasma glycated protein levels is useful for monitoring diabetic control because glycated protein concentrations in serum or plasma reflect an average of blood glucose level over approximately a half month period.

One currently employed assay that provides accurate determinations of blood glycated proteins, levels is the GlyPro™ assay currently marketed by Genzyme Corporation, where this assay is described in U.S. Pat. No. 6,008,006. While this assay provides accurate results, it is performed in a clinical lab by a trained technician with a sophisticated instrument, and is therefore not suitable for home or physician office use.

U.S. Pat. Nos. 5,470,752; 5,695,949 and 5,725,774 describe a multilayer reagent test strip for fructosamine quantification, where the test strip is designed for home or physician office use. However, measurements provided by the test strips described herein tend to be inaccurate, as substances in the fluid sample other than the fructosamine analyte also react with the signal producing system and affect the signal generated thereby, leading to inaccuracies in the ultimate fructosamine quantification achieved with such test strips.

Accordingly, there is continued interest in the development of additional multilayer reagent strips formats that are suitable for glycated protein quantification, where the test strips are suitable for use in the home or physician office and provide for the highly accurate measurements achieved with the currently employed clinical laboratory based protocols.

Relevant Literature

United States Patents of interest include: U.S. Pat. Nos. 5,470,752; 5,695,949; 5,725,774; 6,008,006. Also of interest are: WO 96/31270; WO 96/31619; WO 96/34977; EP 821064; and EP 737744.

SUMMARY OF THE INVENTION

Multilayer reagent test strips for quantitating glycated protein in a fluid sample, as well as methods for using the same, are provided. The subject multilayer test strips include at least a filter layer, a protease layer and a ketoamine oxidase signal producing and fluid flow control system layer. In using the subject test strips, a fluid sample is applied to the test strip and a signal is generated that can be employed to quantitate the glycated protein level in the sample. Also provided are kits and systems that include the subject test strips and find use in practicing the subject methods. The subject compositions and methods find use in glycated protein monitoring applications, among other utilities.

DESCRIPTION OF THE SPECIFIC EMBODIMENTS

Multilayer reagent test strips for quantitating glycated protein in a fluid sample, as well as methods for using the same, are provided. The subject multilayer test strips include at least a filter layer, a protease layer and a ketoamine oxidase signal producing fluid flow control system layer. In using the subject test strips, a fluid sample is applied to the test strip and a signal is generated that can be employed to quantitate the glycated protein level in the sample. Also provided are kits and systems that include the subject test strips and find use in practicing the subject methods. The subject compositions and methods find use in glycated protein monitoring applications, among other utilities.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the cell lines, vectors, and methodologies, which are described in the publications, which might be used in connection with the presently described invention.

As summarized above, the subject invention provides multilayer reagent test strips for quantitating glycated protein in a sample, as well as systems and kits that include the subject test strips. In further describing the invention, the test strips are described first in greater detail, followed by a review of the methods of using the test strips to quantitate glycated protein level. Finally, a review of representative systems and kits according to the subject invention is also provided.

Multilayer Reagent Test Strips

As summarized above, the subject invention provides multilayer reagent test strips, where the subject test strips find use in quantitating glycated protein in a fluid composition, as described in greater detail below. The subject reagent test strips are multilayer reagent test strips, by which is meant that the subject reagent test strips include a plurality of different layers, where the layers are in sequential fluid communication, such that a fluid applied to a first layer of the plurality sequentially travels through the remaining layers of the plurality in a sequential manner.

The number of distinct layers that make up the subject test strips may vary, typically ranging from about 2 to 10, usually from about 3 to 7 in many embodiments. In many embodiments, the subject test strips include a minimum of three different layers, which layers, in sequential order, are: (a) a blood filter layer for separating red blood cells from plasma; (b) a protease layer; and (c) a ketoamine oxidase signal producing and fluid flow control system layer. As such, many embodiments of the subject test strips include at least the above layers in sequential order, such that the second protease layer is in fluid communication with the first blood filter layer and the third ketoamine oxidase layer is in fluid communication with the second protease layer. In many embodiments, one or more additional layers that provide for additional functionality are also present.

Blood Separation Layer(s)

The first element of the subject multilayer test strips is the blood separation element, which element serves to produce plasma from whole blood, where the plasma then flows into subsequent layers for further treatment/analysis. This element may be present as a two layer separation element, or a single layer separation element. Each of these distinct embodiments is described in greater detail below.

Two Layer Blood Separation/Filter Element

In certain embodiments, a two layer structure is employed to produce plasma from whole blood, where the two layer structure includes a blood separation layer and a filter layer, which layers work in tandem to provide for red blood cell free plasma which is subsequently assayed in the subsequent layers. As used herein, the term "plasma" means the substantially colorless fluid obtained from a whole blood sample after red blood cells have been removed by the separation process and device of the present invention. Because plasma is serum plus the clotting protein fibrinogen, the term "plasma" is used broadly herein to include both plasma and serum. The blood separation/filter layers of the subject strips include a separation matrix and a filter layer.

The separation matrix of the present invention is a permeable matrix which does not contain glass fibers and, therefore, is termed "a permeable non-glass fiber matrix." The term "permeable" means liquid-permeable, such as permeable to plasma, as well as permeable or porous to red blood cells when the matrix is provided in the absence of a polyol. As used herein, the phrase "matrix being porous to red blood cells in the absence of a polyol" means that without the polyol contained in or on the matrix the red blood cells would simply pass through the matrix, virtually immediately. In the absence of the polyol, red blood cells are not retained, by filtration or otherwise, in the matrix.

The polyol contained within or on the matrix chemically reacts with the whole blood sample so as to clump the red blood cells. As used herein, "clump" or "clumping" means the collection into a mass or group, red blood cells distributed in a whole blood sample. While not wishing to be bound by any theory or mechanism, the clumping can be the result of agglutination, coagulation, or the like, or some other chemical interaction between the polyol and the red blood cells.

A useful permeable matrix can be a woven or non-woven material and can be an absorbent or a non-absorbent material which may or may not be hydrophilic. Especially suitable materials for the matrix include, for example, woven or non-woven, absorbent or non-absorbent, Nylon, Rayon, cotton, acrylic and polyester. In one embodiment of the invention, the matrix is a non-woven, non-absorbent polyester. The polyester is preferably a poly(paraphenylene terephthalate), such as that used in a preferred polyester sold as Sontara® (DuPont, Inc., Wilmington, Del.). Another preferred matrix is the woven, absorbent Nylon Tetex®3-3710 (Tetko, Inc., Lancaster, N.Y.).

Depending upon the porosity or other properties of the matrix, the clumped red blood cells either are retained in the matrix or are filtered out by the filter material as described below. Some of the above-described matrix materials, such as the non-woven, non-absorbent polyesters, do not have "pores" in the traditional sense, i.e., that can be measured, for example, by pore size (microns). In the absence of a polyol of the present invention such materials essentially have no limit as the porosity and are porous to red blood cells, which have an average size of 5 $\mu$m. With such macroporous materials, if the polyol is not present the red blood cells pass through the matrix almost immediately. For those matrix materials which can be characterized based on pore size, the matrices used in the present invention can have a pore size generally of from about 2 $\mu$m to about 10 $\mu$m. Such pores sizes can be useful for retaining the clumped red blood cells. Depending upon the porosity, thickness, which is generally 200 to 1100 $\mu$m, and other properties of the matrix, such as absorbency, the clumped red blood cells are either retained in the matrix or captured in a final filter material as described below.

The polyol-containing matrix has a first surface for sample application and a second surface where plasma is received or becomes available for additional separation. Generally, the first and second surfaces are presented as opposite sides of the matrix. The whole blood sample flows in a direction from the first surface toward the second surface, under conditions which provide such directional flow, such as, gravitation, vacuum, or external pressure. To enhance the simplicity of the method, if desired, separation can be performed by gravity alone. Preferably, the separation matrix provides for flow in a vertical direction, preferably by gravitation.

The separation method and device include a permeable non-glass fiber matrix containing a polyol. As used herein, the terms "matrix containing a polyol" and "polyol-containing matrix" mean that the polyol is separately added to the matrix and is not a component originally found in the composition or make up of the matrix, such as cellulose filter paper. Further, "matrix containing a polyol" means a polyol can be impregnated into the matrix or coated into or onto the matrix or covalently or non-covalently bound to the matrix. In a preferred embodiment, the polyol is impregnated into the matrix.

As used herein, the term "polyol" means a polyhydroxy alcohol which is an alkyl or aromatic containing more than one hydroxyl group. The term "poly" as used in "polyol" does not infer that the alkyl or aromatic compound is a large polymer made up of repeating monomeric units, but, instead, means that more than one hydroxyl group is present in the compound. As discussed more fully below, with the exception of polysaccharides, the polyols used in the present invention are simple sugars or sugar alcohols, oligosaccharides, or other naturally or non-naturally occurring non-polymeric alkyl or aromatic compounds. Therefore, the term "polyol" encompasses sugars, alcohol derivatives of sugars, herein termed "sugar alcohols," and other naturally or non-naturally occurring non-polymeric polyols.

As used herein, "sugar" includes monosaccharides, oligosaccharides, and polysaccharides. A monosaccharide is a simple sugar which is as a linear, branched, or cyclic polyhydroxy alcohol containing either an aldehyde or a ketone group. Exemplary monosaccharides include, but are not limited to, mannose, glucose, talose, galactose, xylose, arabinose, lyxose, ribose and fructose. An oligosaccharide is a linear or branched carbohydrate that consists from two to ten monosaccharide units joined by means of glycosidic bonds. Oligosaccharides which can be used in the present invention include, but are not limited to disaccharides such as sucrose, trehalose, lactose and maltose. Examples of larger oligosaccharides which can be used in the invention include the cyclodextrins, such as alpha-cyclohexylamylose, beta-cycloheptaamylose, and gamma-cyclooctoamylose, as well as other oligosaccharides well known in the art. A polysaccharide is any linear or branched polymer having more than ten monosaccharides linked together by glycosidic bonds. Exemplary polysaccharides include, but are not limited to, ficoll, polysucrose, and hydroxyethyl starch.

Encompassed within "sugar" are those sugars which are naturally occurring as well as those which are known but which have not yet been identified as occurring naturally in plants or animals. For example, there are five known naturally occurring aldohexoses, including D-glucose, D-mannose, D-talose, D-galactose, and L-galactose. However, the aldohexose structure has four chiral carbons and thus, sixteen possible stereoisomers, all of which are known, although only the five listed above have been identified as occurring naturally in plants or animals. Thus, "sugar" encompasses enantiomers in either the D or L forms of a sugar as well as racemic mixtures thereof.

A polyol of the present invention also can be a "sugar alcohol." A "sugar alcohol" is an alcohol derivative of a mono- or an oligosaccharide which is generally formed by reduction of the aldehyde or ketone moiety on the mono- or oligosaccharide. Exemplary sugar alcohols include, but are not limited to, mannitol, sorbitol, arabitol, inositol, galactitol, erythritol, and threitol. Also included within the definition of "sugar alcohol" are the alcohol derivatives of those mono- and oligosaccharides described above.

Where chiral carbons are present in the sugar alcohol, the sugar alcohol may be in the D or L form, such as D-threitol or L-threitol, or in a racemic mixture of both the D and L forms. The sugar alcohol can, but does not have to, be naturally occurring. That is, the sugar alcohol can be a derivative of a known, naturally occurring sugar, or, alternatively, it can have a D or L configuration known to exist but not necessarily identified as occurring in nature. The sugar alcohol also can be a sugar which is found naturally in its reduced alcohol form or it can be an alcohol derivative of a sugar which derivative is not known to exist in nature.

In addition to sugar or sugar alcohols, the polyol can be a non-polymeric naturally occurring or non-naturally occurring polyol, which includes linear, branched, or cyclic alkyl or aromatic compounds containing more than one hydroxyl group. As used herein the term "non-polymeric" means the alkyl or aromatic compounds are not polymers. Polymers are defined as high molecular weight compounds consisting of long chains that may be open, closed, linear, branched, or crosslinked, which chains are composed of repeating units, called monomers, which may be either identical or different. As used herein, those polyols which are "naturally occurring" are ones which occur in nature and those which are "non-naturally occurring" are not found in nature. Generally, these naturally occurring or non-naturally occurring alkyl or aromatic compounds range in size from three to twenty carbons ($C_3$ to $C_{20}$), and more preferably, from three to ten carbons ($C_3$ to $C_{10}$). Examples of such naturally occurring, non-polymeric polyols are glycerol, a three-carbon trihydroxy alcohol that occurs in many lipids, and quinic acid, 1,3,4,5-tetrahydroxycyclo-hexanecarboxylic acid, which acid can be in the salt form. Examples of non-naturally occurring, non-polymeric polyols include pentaerythritol and dipentaerythritol.

In one embodiment, to apply the polyol to the matrix, the polyol can simply be dissolved in an aqueous solution generally, at a concentration of about 20% when used alone, and at about 10% concentration when combined with a polycationic polymer, which is generally present in a concentration of about 0.5% to 5% as discussed more fully below. If desired, multiple layers of matrices containing polyol at lower concentrations, such as four layers of matrix containing 5% polyol, also can be used. The polyol and, if present, the polycationic polymer can alternatively be dissolved in physiological saline (0.85% NaCl), phosphate buffered saline (PBS), an organic solvent, or the like.

In addition to the polyol, a polycationic polymer can, but does not have to, be added to the matrix. Similar to the addition of a polyol to the matrix, the polycationic polymer can also be physically impregnated, coated into or onto, or covalently or non-covalently bound to the matrix. The polycationic polymer is also useful for clumping, as well as stabilizing clumped, red blood cells.

The polycationic polymer component can be any polymer having more than one cationic site and are generally based on monomers which contain an amine group. Suitable polycationic polymers include, for example, hexadimethrine bromide, trimethylenehexamethylenediammoniumbromide, polylysine, polyallylamine, polyarginine, poly(N,N-dimethylaminoethylmethacrylate, copolymers of N,N-dimethylaminoethylmethacrylate and methylmethacrylate, polyethyleneimine, poly(diallyldimethylammonium chloride), poly(1,1-dimethyl-3,5-dimethylenepiperidinium chloride), and mixtures thereof. The polymerized positively charged amino acids, such as polylysine, can have the amino acids in either the D or L forms, such as poly-L-lysine or poly-D-lysine, or a racemic mixture thereof, such as poly-D,L-lysine.

As described above, in one embodiment, to apply the cationic polymer to the matrix, the polymer can be dissolved in an a solution such as water, physiological saline, PBS, an organic solvent, or the like, and the matrix then dipped into the polymer containing solution. Generally, the polymer is in a concentration of about 0.5% to 5%. Where both polyol and polymer are contained in the matrix, the order of adding polyol and polymer to the matrix is irrelevant. For example, polyol and polymer can be simultaneously or sequentially dissolved in such aqueous solutions or solvents as those described above and both polyol and polymer simultaneously applied to the matrix, as described in the Examples below. Alternatively, polyol and polymer can be applied to the matrix sequentially in any order.

Non-hemolytic detergents, such as Pluronic (Pragmatics, Inc., Elkhart, Ind.), can be added to the aqueous solutions or solvents described above, generally at a concentration of 0.01% to 0.1%. Such detergents help maximize impregnation of a polyol into the matrix, thereby improving the flow rate of the whole blood sample and the plasma. Other optional agents which can further enhance the flow rate, include, for example, polyvinylpyrrolidone or similar polymers and other fillers which give the matrix and the below described filter material stiffness.

In addition, the matrix may include one or more additional reagents to remove interference, e.g., $KIO_3$, $KMnO_4$, $FeSO_4$ for removing ascorbic acid interference, uricase for removing uric acid interference.

As indicated above, a filter material can be used in combination with the matrix of the present invention. Suitable filter materials include, for example, Nylon, cellulose acetate, polysulfone, synthetic fibers, and polycarbonate. The filter can, but does not have to, be a membrane. Illustrative filters and membranes include, for example, BTS polysulfone membrane (Memtek, Inc., San Diego, Calif.), Ahlstrom synthetic fiber sheets, such as 94–30 A (Ahistrom Filtration, Inc., Mt. Holly Spring, Pa.), Biodyne A® Nylon membrane (Pall Corp., East Hills, N.Y.), Ultrabind 450 (Gelman, Ann Arbor, Mich.), and Nucleopore® polycarbonate (Costar, Corp., Cambridge, Mass.).

The need for any additional filter material depends to a large extent on the porosity, thickness, absorbency or other properties of the matrix. For example, the clumped red blood cells, depending upon the above properties of the matrix, can be retained in the matrix. Alternatively, or in addition thereto, a final filter material can be used to capture or retain any additional clumps of red blood cells. Where present, the filter material can generally have a porosity of up to about 12 $\mu$m and preferably will have a pore size of less than 10 $\mu$m, and more preferably 5 $\mu$m or less.

A filter material can be placed underneath the polyol-containing separation matrix, thereby supporting the matrix.

In preferred embodiments of the invention, the blood separation method and device comprise a non-woven, non-absorbent polyester matrix impregnated with mannitol and either a Nylon or polysulfone membrane below the matrix. Preferably, the matrix additionally contains hexadimetlirine bromide and $KIO_3$.

The above-described two layer filtration element is further discussed in U.S. Pat. Nos. 5,470,752; 5,695,949 and 5,725774; the disclosures of which are herein incorporated by reference.

Single Layer Filtration Layer

In other embodiments, blood separation is achieve by an element made up of a single filtration layer. In these embodiments, the single filtration layer is typically a porous matrix, wherein the separation takes place as the sample moves through the matrix from one side to the other. A representative matrix to accomplish that separation may have pores that trap the red blood cells, generally pore sizes in the range from about 0.1 $\mu$m to about 5 $\mu$m. In certain embodiments, the membrane is anisotropic, with a range of pore sizes; e.g., a broad range of pore sizes. When the matrix comprises an anisotropic membrane, the first side to which non-filtered blood is applied may be the large-pore side. For example, a gradient of pore sizes from about 0.1 $\mu$m to about 150 $\mu$m may extend through the membrane. On the large-pore side, pore size is preferably in the range from about 30 $\mu$m to about 40 $\mu$m. On the side of the membrane where the pores are smallest (i.e., the side that fluid exits in order to pass on to the next layer), the void volume is relatively small, and the material of the membrane is generally quite dense, within a layer that can typically constitute up to 20% of the membrane's thickness. Within this layer, pore size is sometimes in the range from about 0.1 to about 0.8 $\mu$m, with a nominal pore size often about 0.3 $\mu$m. In certain embodiments, the matrix is one that not only traps red blood cells but also minimizes lysing of the cells, so that any portion of the sample that passes through the matrix to the downstream layers in the direction of fluid flow does not absorb light to any appreciable extent at about 700 nm.

The matrix of the separation layer is generally a hydrophilic porous membrane. The matrix allows for the flow of an aqueous medium through it. Polysulfones and polyamides (Nylons) are examples of suitable matrix materials.

Other polymers having comparable properties may also be used. A preferred method of preparing the porous material that forms the matrix of the separation layer is to cast the polymer without a supporting core. Such a matrix is, for example, the anisotropic polysulfone membrane available from Memtec, Inc., San Diego, Calif. The terms "matrix" and "membrane" are used interchangeably herein. Each term is understood to not be limited to a single layer and may include, for example, an absorbent layer. A matrix of less than about 500 μm thickness is usually employed with about 115 to 155 μm being preferred. A thickness of about 130 to 140 μm is most preferred, particularly when the matrix is Nylon or anisotropic polysulfone. The matrix generally does not deform on wetting, thus retaining its original conformation and size, and has sufficient wet strength to allow for routine manufacture.

Protease Layer

Downstream from the blood separation element/layer(s) in the direction of fluid flow is the protease layer of the subject multilayer reagent test strips. This layer comprises a matrix or membrane material and a protease enzyme. The matrix material is one that is porous and provides for flow of sample fluid through the material. The matrix that is employed in this layer is typically an inert porous matrix that provides a support for protease component. As such, the matrix is one that is permissive of aqueous fluid flow through it and provides sufficient void space for the protease to exert its activity on proteins present in fluid that passes through the matrix. A number of different porous matrices have been developed for use in various analyte detection assays, which matrices may differ in terms of materials, pore sizes, dimensions and the like, where representative matrices include those described in U.S. Pat. Nos: 55,932,431; 5,874,099; 5,871,767; 5,869,077; 5,866,322; 5,834,001; 5,800,829; 5,800,828; 5,798,113; 5,670,381; 5,663,054; 5,459,080; 5,459,078; 5,441,894 and 5,212,061; the disclosures of which are herein incorporated by reference. The dimensions and porosity of the test strip may vary greatly, where the matrix may or may not have a porosity gradient, e.g., with larger pores near or at the sample application region and smaller pores at the detection region. Examples of specific matrix materials of interest include those prepared from polyamide (Nylon), polysulfone, polyester, polyacrylate, cellulose, polycarbonate, nitrocellulose, etc.

The protease layer also includes a protease, i.e., an enzyme having protease activity. The membrane or matrix of the protease layer is typically coated with the protease in a manner that preserves the activity of the protease. The protease of the protease layer is one that cleaves protein molecules to yield accessible ketoamine bonds. Any convenient protease may be employed, where representative proteases include Protease XIV, Proteinase K, chymotrypsin, substilisin, trypsin, and the like.

Signal Producing and Fluid Flow Control System Layer

In fluid communication with, and downstream of, the protease layer is the ketoamine oxidase signal producing and fluid flow control system layer. This signal producing system layer includes a porous matrix or membrane element, such as those described above, which includes a ketoamine oxidase signal producing system. In the subject test strips, the one or more members of the signal producing system are associated, e.g., covalently or non-covalently attached to, at least a portion of (i.e., the detection region) the matrix, and in many embodiments to substantially all of the porous matrix. In many embodiments, the matrix or membrane component is typically coated with the reagents of the ketoamine oxidase signal producing system.

The ketoamine oxidase signal producing system of this particular layer of the multilayer reagent test strips is an oxidation signal producing system. By oxidation signal producing system is meant that in generating the detectable signal from which the ketoamine concentration in the sample is derived, a ketoamine bond is oxidized by a ketoamine oxidase to produce an oxidized form of the substrate and a corresponding or proportional amount of hydrogen peroxide. The hydrogen peroxide is then employed, in turn, to generate the detectable product from one or more indicator compounds (collectively referred to herein as a chromogen system), where the amount of detectable product produced by the signal producing system, i.e., the signal, is then related to the amount of ketoamine in the initial sample. As such, the ketoamine oxidase oxidation signal producing systems present in the subject test strips are also correctly characterized as hydrogen peroxide based signal producing systems or peroxide producing signal producing systems.

As indicated above, one member of the subject signal producing systems is a ketoamine oxidase. Ketoamine oxidases of interest for use in the subject reagent systems are those that specifically oxidize the ketoamine bond to produce an oxidized substrate and a corresponding amount of hydrogen peroxide, where by corresponding amount is meant that the amount of hydrogen peroxide that is produced is proportional to the amount of ketoamine present in the sample. A variety of different suitable ketoamine oxidases are known to those of skill in the art and may be employed in the subject invention, where representative ketoamine oxidases of interest include those described in U.S. Pat. Nos. 5,712,138 and 6,008,006, the disclosures of which are herein incorporated by reference, as well as in EP 821064 and EP 737744.

In addition to the ketoamine oxidase activity of the signal producing system, the signal producing system also includes one or more indicator compounds, collectively referred to herein as a chromogen system, where the chromogen system produces a chromogenic product in the presence of hydrogen peroxide.

The signal producing systems also include an enzyme that catalyzes the conversion of a dye substrate into a detectable product in the presence of hydrogen peroxide, where the amount of detectable product that is produced by this reaction is proportional to the amount of hydrogen peroxide that is present. This second enzyme is generally a peroxidase, where suitable peroxidases include: horseradish peroxidase (HRP), soy peroxidase, recombinantly produced peroxidase and synthetic analogs having peroxidative activity and the like. See e.g., Ci et al. (1990) *Analytica Chimica Acta*, 233:299–302.

The dye substrates are oxidized by hydrogen peroxide in the presence of the peroxidase to produce a product that absorbs light in a predetermined wavelength range, i.e., an indicator dye. Preferably the indicator dye absorbs strongly at a wavelength different from that at which the sample or the testing reagent absorbs strongly. The oxidized form of the indicator may be the colored, faintly-colored, or colorless final product that evidences a change in color of the testing side of the membrane. That is to say, the testing reagent can indicate the presence of an analyte in a sample by a colored area being bleached or, alternatively, by a colorless area developing color.

Dye substrates that are useful in the present invention include urea derivative dyes. Urea derivative dyes include at least some of those disclosed in JP 1118768; JP 9019296; EP 38 205, EP 124 287 and EP 251297; the disclosures of which are herein incorporated by reference. The dye substrate is generally a urea derivative, having a negative charge, where suitable negatively charged urea derivatives include those bearing a carboxylate group or a sulfonate group. Urea derivative dyes of interest are represented by the following formula:

R¹R²NMCONHR³, wherein

R¹, R² taken together is a N, N-di-substituted aminoaryl; and

R³ is selected from the group consisting of carboxyalkyl, alkoxycarbonyl, alkylcarbonyl, arylsulfonyl, sulfoaryl and carboxyaryl.

The aryl groups of R¹ and R² may be bonded via S to become a phenothiazine derivative type of dye, which is represented by the following formula:

wherein R⁴ and R⁵ are independently selected from NR₂ and OR, where R is hydrogen, ($C_1$–$C_6$)-alkyl, ($C_1$–$C_6$)-alkenyl, aryl, substituted aryl, arylalkyl, substituted arylalkyl; R³ is defined above; and R⁶ and R⁷ are independently selected from hydrogen, ($C_1$–$C_6$)-alkyl, ($C_1$–$C_6$)-alkenyl, acyl, carboxyl, sulfonyl, nitro, halogen, hydroxyl, ($C_1$–$C_6$)-alkoxyl or hydroxy-($C_1$–$C_6$)-alkyl.

Alternatively, the aryl groups of R¹ and R² may be bonded via O, to form a phenoxazine derivative type of dye, which is represented by the following formula:

In yet another embodiment, the aryl groups of R¹ and R² is not bonded, which is represented by the following diphenylamine formula:

Exemplary urea derivative dyes include 10-(carboxymethylaminocarbonyl)-3,7-bis(dimethylamino) phenothiazine (leuco methylene blue), 10-(carboxymethylaminocarbonyl)-4,4'-bis(dimethylamino) diphenylamine, 10-propionic acid phenothiazine, and salts thereof. In a preferred embodiment, the urea derivative dye is 10-(carboxymethylaminocarbonyl)-3,7-bis(dimethylamino)phenothiazine, sodium salt.

A particularly preferred ketoamine oxidase signal producing system layer is one that includes the layer described in U.S. application Ser. No. 09/593,827 (the disclosure of which is herein incorporated by reference) which includes a ketoamine oxidase, as described above.

In many embodiments, the ketoamine oxidase signal producing system layer is a hydrophobic layer which retards entry of aqueous materials into the layer, such that the plasma fraction of the sample which is being assayed on the strip resides in the protease layer for a period of time that is longer than if the signal producing system layer were not rendered hydrophobic, e.g., by a time period that is at least about 5 times longer, typically at least about 10 times longer. This feature of the signal producing system layer assures that the plasma is present in the protease layer for a period of time sufficient for the protease to cleave the proteins present in the plasma sufficiently to yield accessible ketoamine.

The signal producing system layer may be rendered hydrophobic using any convenient protocol. One protocol of particular interest is that described in U.S. Pat. No. 6,743,596 filed on even date herewith and entitled "Multilayer Reagent Test Strips That Include at Least One Fluid Flow Control Layer Methods for Using the Same," the disclosure of which is herein incorporated by reference. In this protocol, the porous matrix that includes the signal producing system is coated with an organic solvent, e.g., by dipping the membrane in an organic solvent.; Organic solvents of interest include, but are not limited to: chloroform, dichloromethane, halogenated hydrocarbon, hydrocarbon, ethyl acetate, and the like. Another protocol of interest for rendering the signal producing system hydrophobic is one that coats the membrane with a fatty acid or other fluid retention agents, such as described in U.S. Pat. No. 5,447,689, the disclosure of which is herein incorporated by reference.

Additional Layers

In addition to the above specific filter, protease and ketoamine oxidase signal producing system layers, the subject multilayer reagent test strips may also include a number of additional layers.

Placed above the above-described layers may be a mesh layer which serves to hold all of the subsequent or underlying layers together. The mesh layer may be fabricated from any convenient material, such as an inert matrix material, as described above. In addition, a clear polymeric, e.g., polyester or analogous polymeric material, layer may be present beneath the signal producing system layer, which layer serves to enhance plasma flow and protect the plasma sample from drying prior to completion of the assay.

Figure 1:
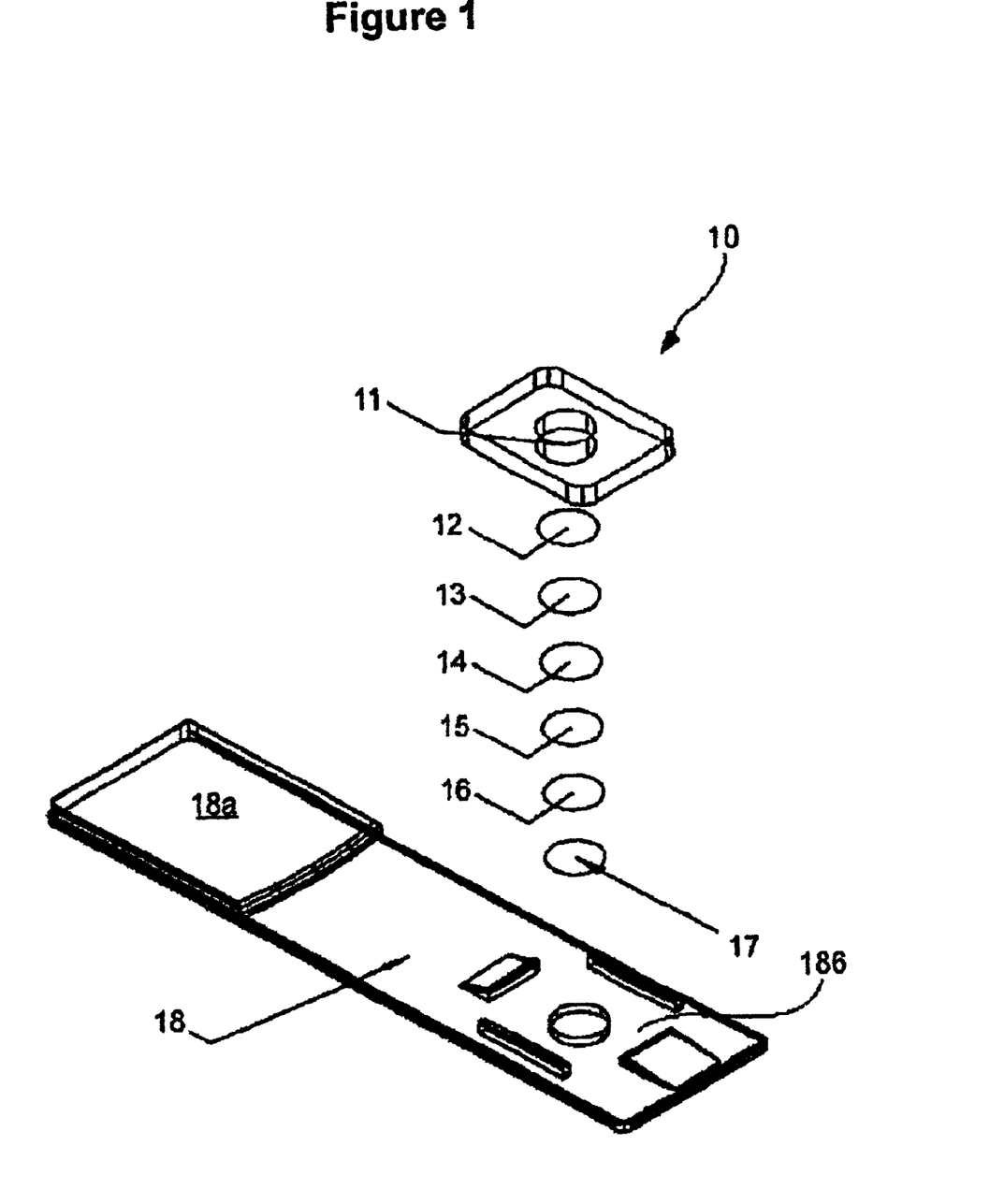
FIG. 1 provides an exploded view of a multilayer reagent test strip according to one embodiment of the subject invention.

The above layers are often present in a "stacked" configuration, as shown in FIG. 1, and may be present in a chamber bounded by an upper guard piece and a support element.

Representative Illustrated Embodiment

FIG. 1 provides an exploded view of a multilayer test strip according to the subject invention. In FIG. 1, multilayer reagent test strip 10 includes injection molded guard element 11 on top of mesh layer 12, which in turn is present above separation layer 13 and filter layer 14, which together make up the blood separation element. Immediately beneath the separation element is the protease layer 15. Beneath protease layer 15 is signal producing layer 16, which is present over polymeric film layer 17. The above layers are present on support element 18, which includes a manual holding region 18a and a sample assay region 18b.

As can be seen in FIG. 1, each of the distinct layers is a disc shaped layer, where the separated layers are placed one on top of the other in a stacked configuration. In many embodiments, the surface area of each of the disparate layers typically ranges from about 0.1 cm$^2$ to about 0.25 cm$^2$, usually from about 0.125 cm$^2$ to about 0.18 cm$^2$, such that the disc shaped layers in the embodiment shown in FIG. 1 generally have a diameter ranging from about 0.35 cm to about 0.6 cm, usually from about 0.4 cm to about 0.5 cm.

The overall dimensions of the support element 18 are selected to provide for a convenient hand held device, such that the support element has a width that typically ranges from about 0.25 in to about 0.7 in, usually from about 0.4 in to about 0.55 in, and a length that ranges from about 1.5 in to about 3 in, usually from about 2 in to about 2.5 in.

The injection molded guard element 11 typically has a width ranging from about 0.18 in to about 0.5 in, usually from about 0.3 in to about 0.38 in and a length ranging from about 0.35 in to about 0.68 in, usually from about 0.45 in to about 0.56 in.

Test Strip Fabrication

The subject reagent test strips may be fabricated employing any convenient protocol. Typically, the various layers are fabricated separately, e.g., by using conventional dipping protocols in one or more reagent solutions, and then assembled into a final test strip. A representative fabrication protocol is provided in the experimental section, infra.

Methods Of Glycated Protein Detection

The above described multilayer reagent test strips find use in methods of detecting the presence of, and often the amount of ketoamine group on protein in a sample. While in principle the subject methods may be used to determine the presence, and often concentration, of ketoamine groups in a variety of different physiological samples, such as urine, tears, saliva, and the like, they are particularly suited for use in determining the concentration of ketoamine groups in blood or blood fractions, e.g., blood derived samples, and more particularly, in whole blood.

An important feature of the subject methods is the use of the subject signal producing systems that include a urea derivative dye provides for the highly sensitive detection of hydrogen peroxide. As such, hydrogen peroxide may be detected at submillimolar concentrations using the subject stable dry reagent formats, e.g., test strips, where by submillimolar concentration is typically meant concentrations ranging from 0.010 to 1 mM, usually from about 0.050 to 0.8 mM. Use of the subject signal producing systems that include a urea derivative dye provides for more sensitive detection of hydrogen peroxide as compared to signal producing systems that include a dye substrate other than a urea derivative dye, e.g., N-ethyl-N-(2-hydroxy-3-sulfopropyl)-3-methylaniline, 4-aminoantipyrine.

In practicing the subject methods, the first step is to apply a quantity of the physiological sample to the test strip, where the test strip is described supra. The amount of physiological sample, e.g., blood, that is applied to the test strip may vary, but generally ranges from about 2 μL to 40 μL, usually from about 5 μL to 20 μL. Because of the nature of the subject test strip, the blood sample size that is applied to the test strip may be relatively small, ranging in size from about 2 μL to 40 μL, usually from about 5 μL to 20 μL. Where blood is the physiological sample, blood samples of a variety of different hematocrits may be assayed with the subject methods, where the hematocrit may range from about 20% to 65%, usually from about 25% to 60%.

Following application of the sample to the test strip, the sample is allowed to flow sequentially through the various layers of the strip, such that it separates in the separation element, is digested in the protease layer and reacts with the members of the signal producing system in the signal producing system layer to produce a detectable product that is present in an amount proportional to the initial amount of the ketoamine groups of interest present in the sample. The amount of detectable product, i.e., the signal produced by the signal producing system, is then determined and related to the amount of glycated protein in the initial sample.

Utility

The above-described methods find use in any application where one wishes to test a fluid sample to determine the concentration of ketoamine group on protein present therein. Of particular interest is use of the subject methods to determine/monitor blood glucose levels. In such applications, the detected ketoamine group concentration provided by the subject methods is employed to determine the amount of glycated protein in the tested sample, as is known in the art, which is turn is employed to monitor blood glucose levels, e.g., as is desirable in the treatment and management of patients suffering from diabetes. Utilities for the subject test strips are further described in U.S. Pat. Nos. 5,470,752; 5,695,949; 5,725,774; and 6,008,006; the disclosures of which are herein incorporated by reference.

Detection Systems

Detection systems useful for practicing the subject methods include a reagent test strip as described above and an signal detection instrument or reader. In such systems, a physiological sample is applied to the test strip as described above and the signal produced by the signal producing system is detected and related to the presence (and often the amount) of glycated protein in the sample by the instrument. The above described reaction, detection and relation steps, and instruments for practicing the same, are further described in U.S. Pat. Nos. 4,734,360; 4,900,666; 4,935, 346; 5,059,394; 5,304,468; 5,306,623; 5,418,142; 5,426, 032; 5,515,170; 5,526,120; 5,563,042; 5,620,863; 5,753, 429; 5,573,452; 5,780,304; 5,789,255; 5,843,691; 5,846, 486; 5,902,731; 5,968,836 and 5,972,294; the disclosures of which are herein incorporated by reference. In the relation step, the derived glycated protein concentration takes into account the constant contribution of competing reactions to the observed signal, e.g., by calibrating the instrument accordingly.

Kits

Also provided by the subject invention are kits for use in practicing the subject methods. The kits of the subject invention include a reagent test strip, as described above, and at least one of a means for obtaining said physiological sample, e.g., a lance for sticking a finger, a lance actuation means, and the like, and an standard, e.g., an glycated protein control solution that contains a standardized concentration of ketoamine or precursor thereof, e.g., glycated protein. In certain embodiments, the kits also include a detection instrument, as described above, for detecting the amount of product produced on the strip following sample application and relating the detected product to the presence (and often the amount) of analyte in the sample. Finally, the kits include instructions for using the subject kit components in the determination of glycated protein concentration in a physiological sample. These instructions may be present on one or more of the packaging, a label insert, containers present in the kits, and the like.

The following examples are offered by way of illustration and not by way of limitation.

EXAMPLES

I. Reagent Test Strip Preparation

A: Blood Separation Layer

Mesh: A Tetko mesh #7-280/44 was placed in detergent solution of 1% Pluronic (Pragmatics. Inc.) for one minute. Excess detergent was removed and the mesh was dried by heating at 60° C. for 10 minutes.

Blood separation matrix: A solution containing 10% mannitol, 1.25% hexadimethrine bromide and 1% $KIO_3$ in physiological saline (0.85% NaCl) was impregnated onto Sontara® #8007 (DuPont. Inc.) on an automated impregnation/drying unit (AFM Engineering. Santa Anna. Calif.). The drying temperature was 100° C. for approximately 10 minutes.

Memtec polysulfone membrane was untreated

B: Digestion Layer 200 mg/ml of protease XIV (Sigma) was dissolved in 100 mM EPPS, pH 8.0. The Nylon mesh 3-200/39(SEFAR) was immersed into the protease XIV solution. Excess solution was removed and the mesh was dried by heating at 56° C. for 10 minutes.

A dip: It contains 300 U/ml of KAO in 20 mM PBS, pH 7.4, 1 mg/ml HRP, 1% PVP (MW=360K) and 50 mg/ml mannitol. The Nylon membrane (Pall) was dipped into the solution and the excess solution was removed and the membrane was dried by heating at 56° C. for 5 minutes.

B dip: After A dipping, the Nylon membrane was further dipped into B dip containing 1 mM DA-60 in 70% methanol. The dipped membrane was dried by heating at 56° C. for 5 minutes.

C dip: A and B dipped membrane was quickly pull through into dichloromethane solvent. Excess solvent was removed and the membrane was dried under ventilation hood at room temperature for 2 minutes.

D: Assembly of Test Strip

Each layer was cut into 0.476 cm (3/16 in) diameter discs which were assembled in sequence as indicated in FIG. 1 into final strip.

II. Glycated Protein Assay Employing the Reagent Test Strip as Prepared in Example I.

Figure 2:
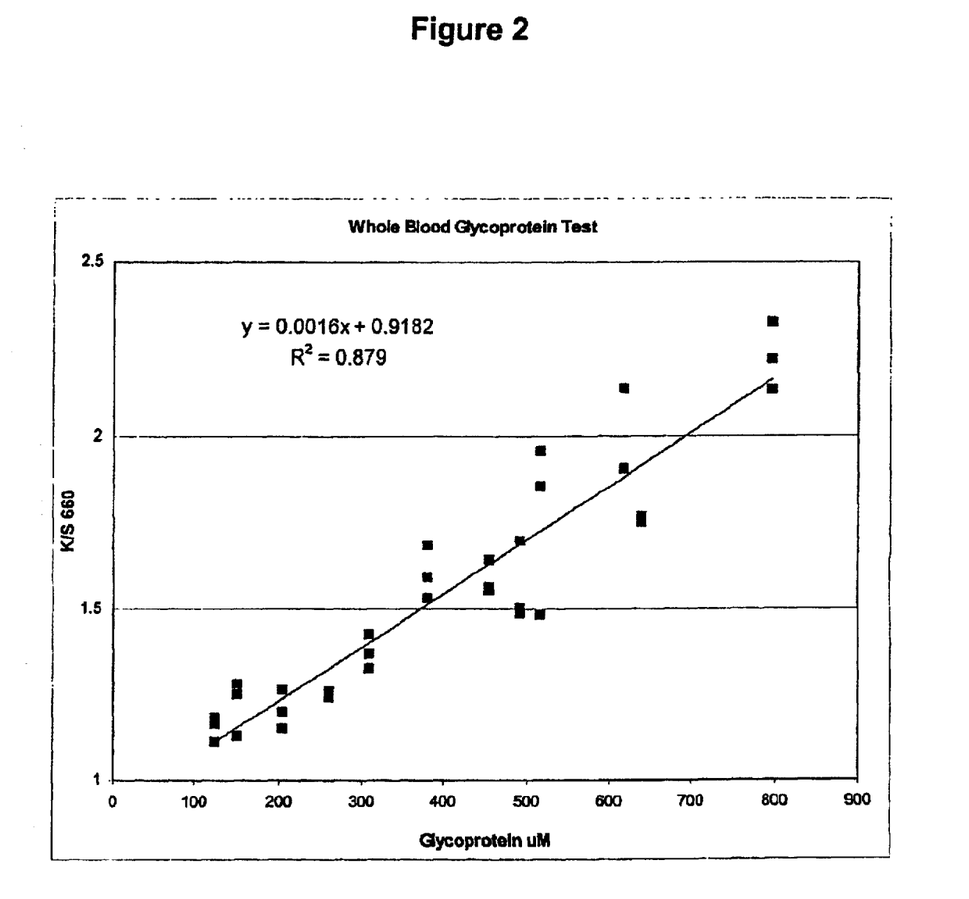
FIG. 2 provides graphical results of an assay performed with test strip with a one-layer blood separation layer configuration.

FIG. 2: One layer blood separation layer strip design was used. i.e., blood separation layer has polysulfone membrane only. 15 μl of whole patient blood was applied to test strip and the test strip was incubated at 37° C. for 5 minutes, then the color intensity was read on the Macbeth reflectance spectrometer.

Figure 3:
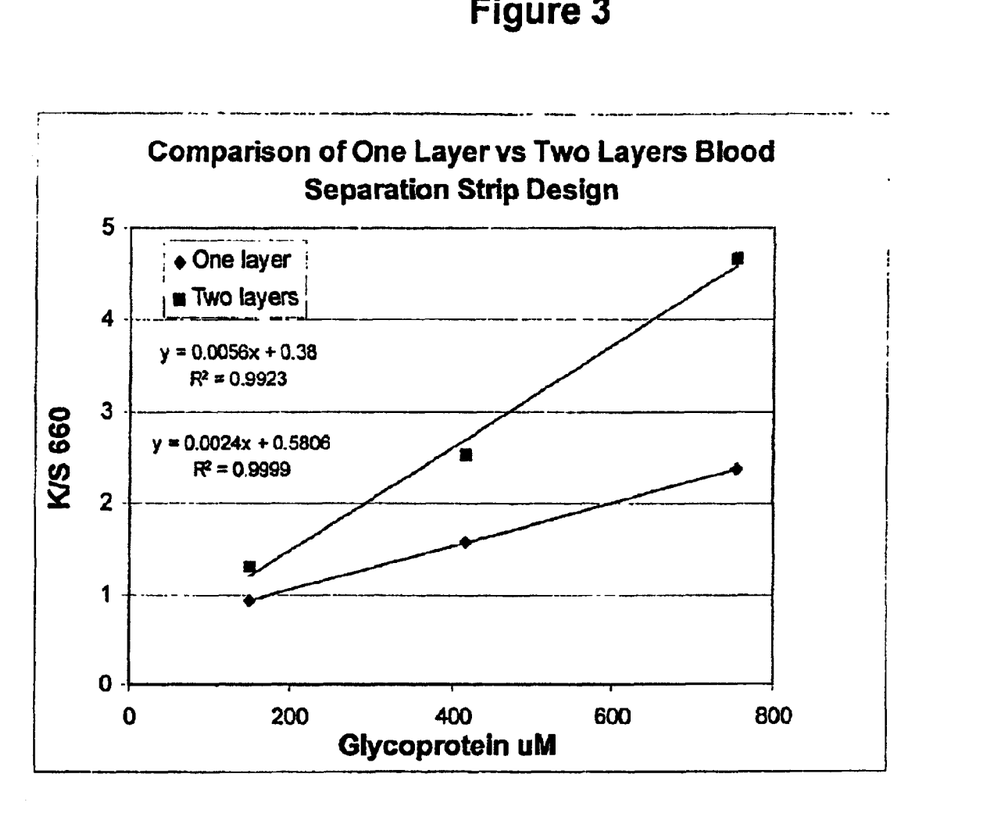
FIG. 3 provides graphical results of an assay with a two-layer blood separation layer configuration.

FIG. 3: Comparison of one layer vs. two layer blood separation strip design. One layer is polysufone membrane only as blood separation layer. Two layers consist of Sontara® filter material and polysulfone membrane both. 15 μl of whole blood with low, medium and high level glycoprotein was applied to test strip. The strip was incubated at 40° C. for 5 minutes. The color intensity was read on a Macbeth reflectance spectrometer. Significant increase of the slope of color intensity among different level of glycoprotein in two layer strip design definitely gives better resolution range. All data points in the FIG. 3 represent the average of eight replicates and CV is around 10% for both strips.

It is evident from the above results and discussion that the subject invention provides a highly sensitive and accurate glycated protein detection system which is capable of providing results that are comparable in reliability and accuracy to those currently achieved only in the clinical laboratory setting, where the system is one that can be employed by a patient or doctor in a non laboratory setting, e.g., at home or in the doctor's office. As such, the subject invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A multilayer test strip for quantitating glycated protein in a fluid sample, the test strip comprising:

a blood separation element for separating red blood cells from plasma;

a protease layer in fluid communication with said blood separation element; and a ketoamine oxidase signal producing system layer in fluid communication with said protease layer.

2. The multilayer test strip according to claim 1, wherein said ketoamine oxidase signal producing system layer is hydrophobic.

3. The multilayer test strip according to claim 2, wherein said layers of the multilayer test strip are present in a stacked configuration.

4. The multilayer test strip according to claim 3, wherein said stacked layers are present in a chamber of a support element bounded by a substrate strip.

5. The multilayer test strip according to claim 1, wherein said protease layer comprises a porous matrix and a protease that cleaves proteins to produce ketoamine oxidase accessible ketoamine bonds.

6. The multilayer test strip according to claim 5, wherein said protease is protease XIV.

7. The multilayer test strip according to claim 1, wherein said ketoamine oxidase signal producing system layer comprises a porous matrix, a ketoamine oxidase, a peroxidase and at least one indicator compound.

8. The multilayer test strip according to claim 7, wherein said porous matrix of said ketoamine oxidase signal producing system layer is positively charged.

9. The multilayer test strip according to claim 8, wherein said positively charged porous matrix comprises a material selected from the group of a woven absorbent material, a woven non-absorbent material, a non-woven absorbent material and a non-woven non-absorbent material.

10. The multilayer test strip according to claim 7, wherein said indicator compound comprises a urea derivative dye.

11. The multilayer test strip according to claim 10, wherein said urea derivative dye is a negatively charged urea derivative dye.

12. The multilayer test strip according to claim 11, said urea derivative dye has the formula:

$R^1R^2NCONHR^3$, wherein $R^1$, $R^2$ taken together is a N, N-di-substituted aminoaryl and $R^3$ is selected from the group consisting of carboxyalkyl, alkoxycarbonyl, alkylcarbonyl, arylsulfonyl, sulfoaryl and carboxyaryl.

13. The multilayer test strip according to claim 12, wherein said urea derivative dye is selected from group consisting of phenothiazine derivative dyes, phenoxazine derivative dyes and diphenylamine derivative dyes.

14. The multilayer test strip according to claim 13, wherein said urea derivative dye is 10-(carboxymethylaminocarbonyl)- 3,7-bis(dimethylamino) phenothiazine or a salt thereof.

15. The multilayer test strip according to claim 7, wherein said peroxidase is horseradish peroxidase.

* * * * *

UNITED STATES PATENT AND TRADEMARK OFFICE
CERTIFICATE OF CORRECTION

PATENT NO. : 6,951,728 B2
DATED : October 4, 2005
INVENTOR(S) : Qian et al.

It is certified that error appears in the above-identified patent and that said Letters Patent is hereby corrected as shown below:

Title page,
Item [75], Inventors, "Shery" should be -- Sherry --.

Column 8,
Line 8, "Ahistrom" should be -- Ahlstrom --.
Line 29, "hexadimetlirine" should be -- hexadimethrine --.
Line 36, "achieve" should be -- achieved --.

Column 9,
Line 33, "55,932,431" should be -- 5,932,431 --.

Column 11,
Line 7, "$R^1R^2NMCONHR^3$" should be -- $R^1R^2NCONHR^3$ --.

Column 12,
Line 27, "solvent.;" should be -- solvent. --.
Line 29, "dichioromethane" should be -- dichloromethane --.

Column 13,
Line 11, "about 0.4 in" should be -- about 0.45 in --.

Column 14,
Line 21, "an" should be -- a --.
Line 44, "an" should be -- a -- (both instances).

Column 15,
Line 21, "pull" should be -- pulled --.

Signed and Sealed this

Twenty-first Day of February, 2006

JON W. DUDAS
*Director of the United States Patent and Trademark Office*